United States Patent [19]

Mewshaw et al.

[11] Patent Number: 5,760,070
[45] Date of Patent: Jun. 2, 1998

[54] 4-AMINOETHOXY INDOLONE DERIVATIVES

[75] Inventors: Richard Eric Mewshaw, Princeton, N.J.; Michael Byron Webb, Levittown, Pa.

[73] Assignee: American Home Products Corporation, Madison, N.J.

[21] Appl. No.: 909,799

[22] Filed: Aug. 12, 1997

Related U.S. Application Data

[60] Provisional application No. 60/024,667, Aug. 27, 1996.

[51] Int. Cl.⁶ .................. A61K 31/40; C07D 409/12
[52] U.S. Cl. ............................. 514/414; 548/467
[58] Field of Search ........................ 548/467; 514/414

[56] References Cited

U.S. PATENT DOCUMENTS 5,665,723  9/1997  Hartman et al. ................ 514/255

*Primary Examiner*—Patricia L. Morris
*Attorney, Agent, or Firm*—Rebecca R. Barrett

[57] ABSTRACT

A compound of the formula I:

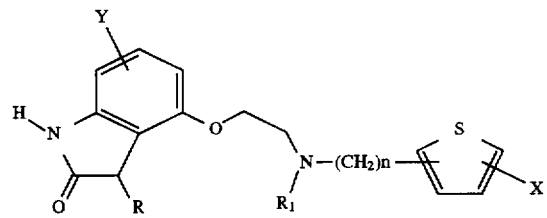

in which Y is hydrogen, halogen or alkoxy; R is hydrogen or alkylthio; $R_1$ is hydrogen or alkyl; X is hydrogen, halogen, alkoxy, alkyl or phenyl; n is one of the integers 1, 2, 3 or 4; or a pharmaceutically acceptable salt thereof are inhibitors of dopamine synthesis and release, useful in the treatment of schizophrenia, Parkinson's Disease, Tourette's Syndrome, alcohol addiction, cocaine addiction, and addiction to analogous drugs.

10 Claims, No Drawings

4-AMINOETHOXY INDOLONE DERIVATIVES

BACKGROUND OF INVENTION

This application claims the benefit of U.S. Provisional Application No. 60/024,667, filed Aug. 27, 1996.

Efforts to induce antipsychotic activity with dopamine autoreceptor agonists have been successful (Dorsini et al. Adv. Biochem. Psychopharmacol 16, 645–648, 1977; Tamminga et al. Science 200, 567–568, 1975; and Tamminga et al. Psychiatry 398–402, 1986). A method for determining intrinsic activity at the dopamine D2 receptor was recently reported [Lahti et al., Mol. Pharm. 42, 432–438, (1993)]. Intrinsic activity is predicted using the ratio of the "low-affinity agonist" (LowAg) state of the receptor and the "high-affinity agonist" (HighAg) state of the receptor, i.e. LowAg/HighAg. These ratios correlate with the agonist, partial agonist, and antagonist activities of a given compound, which activities characterize a compounds ability to elicit an antipsychotic effect.

U.S. Pat. No. 4,314,944 to Huffman and Wilson describes a series of indolones which are useful for cardiovascular abnormalities. NL-009247 describes a series of 2-hydroxy-3-aminopropoxy) oxindoles which are useful as β-adrenergic blocking agents for the treatment of heart diseases and WO 9403425 discloses a series of heterocyclic derivatives useful in the treatment of cardiovascular diseases.

DESCRIPTION OF THE INVENTION

In accordance with this invention, there is provided a group of compounds which have potency at the dopamine $D_2$ receptor. These compounds are depicted by the following Formula I:

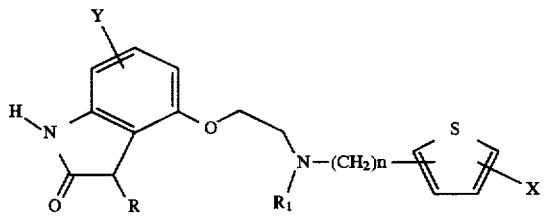

The compounds of this invention are useful antipsychotic agents essentially free from extrapyramidal side effects (EPS). The compounds of this invention are dopamine agonists exhibiting various degrees of intrinsic activity, some of which are selective autoreceptor agonists, and therefore partial agonist (i.e. activate only autoreceptors versus postsynaptic $D_2$ dopamine receptors). As such, they provide functional modulation of the dopamine systems of the brain without the excessive blockade of the postsynaptic dopamine receptors which have been observed to be responsible for the serious side effects frequently exhibited by agents found otherwise clinically effective for the treatment of schizophrenia. Activation of the dopamine autoreceptors results in reduced neuronal firing a well as inhibition of dopamine synthesis and release and therefore provide a means of controlling hyperactivity of the dopaminergic systems. The compounds of this invention were also found to have high intrinsic activity and therefore they can behave as the natural neurotransmitters i.e. as full agonists. As such, they are useful in the treatment of diseases having abnormal concentrations of dopamine in that they can be used as dopamine surrogates in the treatment of disease states such as Parkinson's disease.

More specifically, the compounds of this invention are 4-aminoethoxy-1, 3-dihydro-indol-2-one derivatives which are illustrated by Formula I.

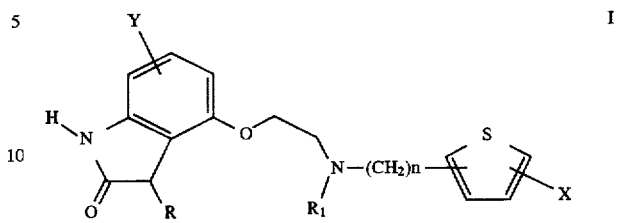

in which:

Y is hydrogen, halogen or alkoxy of 1 to 6 carbon atoms;

R is hydrogen or alkylthio of 1 to 6 carbon atoms;

$R_1$ is hydrogen or alkyl of 1 to 6 carbon atoms;

X is hydrogen, halogen, alkoxy of 1 to 6 carbon atoms, alkyl of 1 to 6 carbon atoms or phenyl;

n is one of the integers 1, 2, 3 or 4;

or a pharmaceutically acceptable salt thereof.

A preferred group of compounds are those in which Y is hydrogen, chloro or fluoro; R is hydrogen or alkylthio of 1 to 3 carbon atoms; R1 is hydrogen or alkyl of 1 to 3 atoms; X is hydrogen and n is on to the integers 2 and 3; or a pharmaceutically acceptable salt thereof.

The compounds of this Formula I also may be used in the form of a pharmaceutically acceptable acid addition salt having the utility of the free base. Such salts, prepared by methods well known to the art are formed with both inorganic or organic acids, for example: fumaric, maleic, benzoic, ascorbic, pamoic, succinic, bismethylenesalicylic, methanesulfonic, ethanedisulfonic, acetic, oxalic, propionic, tartaric, salicyclic, citric, gluconic, lactic, malic, mandelic, cinnamic, citraconic, aspartic, stearic, palmitic, itaconic, glycolic, p-aminobenzoic, glutamic, benzene-sulfonic, hydrochloric hydrobromic, sulfuric, cyclohexylsulfamic, phosphoric and nitric acids.

The compounds of Formula I are generally prepared by the overall sequence indicated in Schemes I and II as follows:

Scheme I

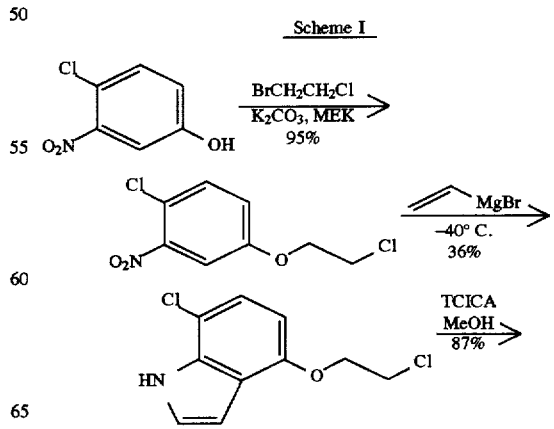

3
-continued
Scheme I

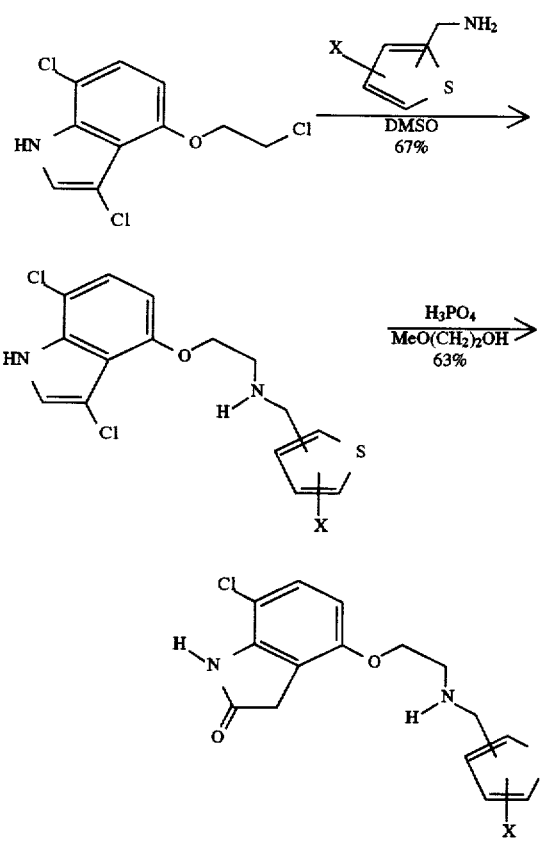

Scheme II

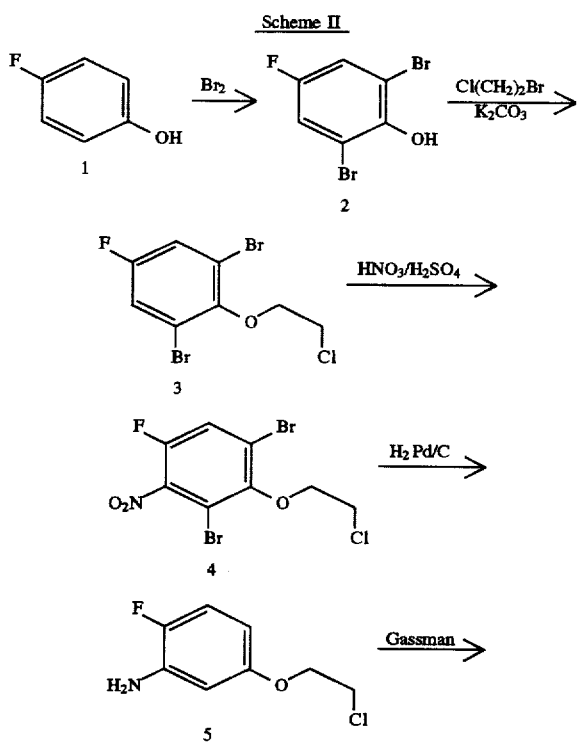

4
-continued
Scheme II

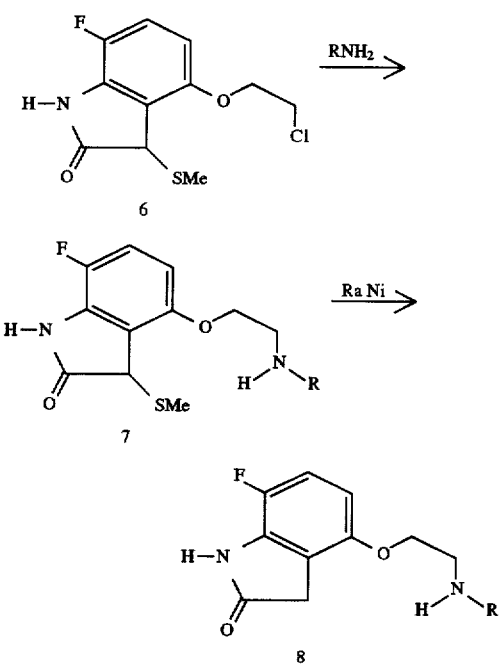

The following examples of the compounds of this invention and their production are presented by way of illustration rather than limitation on the true scope of the invention.

INTERMEDIATE 1

1-(2-Chloroethoxy)-4-chloro-3-nitrobenzene

Method A

To a 2 L 3-neck round-bottom flask was added 4-chloro-3-nitro-phenol (50 g, 0.29 mol), potassium carbonate (100 g, 0.72 mol), dichloroethane (315 g, 3.2 mol), potassium iodide (5 g) and 2-butanone (1 L). The mixture was mechanically stirred and heated to reflux for 44 hours then allowed to cool to room temperature and the solids were filtered. The solvent was evaporated under vacuum and the oil dissolved in diethyl ether (300 mL) and washed with 10% sodium hydroxide. The organic layer was dried over anhydrous magnesium sulfate, filtered, and the solvent removed under vacuum. The product was dissolved in 1:1 methylene chloride-hexanes and filtered through silica. Upon concentration 54.5 g (78.% %) of product was afforded as a white solid: mp 46°–48 ° C.; MS EI m/e 235, 237, 239 (M+); $^1$H NMR (400 MHz, DMSO-$d_6$) δ 3.95 (t, 2H, J=5.2 Hz), 4.36 (t, 2H, J=5.2 Hz), 7.32 (dd, 1H, J=3.2, J=8.9 Hz), 7.66, (d, 1H, J=9 Hz), 7.69, (d, 1H, J=3.2 Hz).

Elemental analysis for $C_8H_7Cl_2NO_3$ Calcd: C, 40.71; H, 2.99; N, 5.93 Found: C, 40.89, H, 2.70; N, 5.83

INTERMEDIATE 1

1-(2-Chloroethoxy)-4-chloro-3-nitrobenzene

Method B

To a 500 mL 3-neck round-bottom flask was added 4-chloro-3-nitro-phenol (10 g, 0.058 mol), potassium carbonate (20 g, 0.14 mol), bromochloroethane (34.5 g, 0.24 mol) and 2-butanone (200 mL). The mixture was mechanically stirred and heated to reflux for 20 hours under nitrogen then allowed to cool to room temperature and the solids were filtered. The solvent was evaporated under vacuum and the oil dissolved in diethyl ether (300 mL) and washed with 10% sodium hydroxide. The organic layer was dried over anhydrous magnesium sulfate, filtered and the solvent removed under vacuum. The product was dissolved in 1:1 methylene chloride-hexanes and filtered through a short pad silica. Upon concentration and standing 12.9 g (94.8.% %) of light yellow crystalline solid was afforded: mp 46°–48° C.; MS EI m/e 235, 237, 239 (M+); $^1$H NMR (400 MHz, DMSO-d$_6$) δ 3.95 (t, 2H, J=5.2 Hz), 4.36 (t, 2H, J=5.2 Hz), 7.32 (dd, 1H, J=3.2, J=8.9 Hz), 7.66, (d, 1H, J=9 Hz), 7.69, (d, 1H, J=3.2 Hz).

Elemental analysis for $C_8H_7Cl_2NO_3$ Calcd: C, 40.71; H, 2.99; N, 5.93 Found: C, 40.89, H, 2.70; N, 5.83

INTERMEDIATE 2

7-Chloro-4-(2-chloroethoxy)-1H-indole

To a solution of 1-(2-chloroethoxy)-4-chloro-3-nitrobenzene (10.00 g, 0.04236 mol) in THF (230 mL) stirred in a cold bath at −50° to −40° C. was added a THF solution of vinylmagnesium bromide (132 mL, 1.0M, 0.132 mol) over 2 minutes. After stirring in the cold bath for 2–2.5 hours, saturated NH$_4$Cl (150 mL) was added to the cold solution and it was removed from the cold bath. 1M HCl was added to dissolve the precipitated solids and the mixture was stirred for 0.5 hour. The layers were separated and the aqueous phase was extracted once with diethyl ether (80 mL). The organic layer combined and dried over anhydrous magnesium sulfate, filtered and the solvent evaporated to give 15.43 g of a dark oil. Purification by chromatography (hexanesmethylene chloride, 2:1) afforded a solid which was triturated with hexane and filtered to afford the product as yellowish white solid: 3.51 g (36%); mp 73–°75 ° C.; MS EI m/e 229, 231, 233 (M+); $^1$H NMR (400 MHz, DMSO-d$_6$) δ 3.99 (t, 2H;, J=5.1 Hz), 4.34 (t, 2H, J=5.0 Hz), 6.51 (t, 1H, J=2.7 Hz), 6.53 (d, 1H, J=7.8 Hz), 7.04 (d, 1H, J=8.0 Hz), 7.29 (t, 1H, J=2.7 Hz), 11.43 (s, 1H).

Elemental analysis for $C_{10}H_9Cl_2NO$ Calcd: C, 52.20; H, 3.94; N, 6.09 Found: C, 52.09; H, 3.92; N, 5.96

INTERMEDIATE 3

Method A 3,7-Dichloro-4-(2-chloroethoxy)-1H-indole

To a solution of 7-chloro-4-(2-chloroethoxy)-1H-indole (4.61 g, 20.0 mmol) in acetonitrile (100 mL) was added N-chlorosuccimide (2.94 g, 2.20 mmol) at room temperature, the reaction was allowed to stir for 1.5 h then poured into water (100 mL) and extracted with methylene chloride (200 mL). The organic layer was dried over anhydrous magnesium sulfate, filtered, and the solvent removed under vacuum to afford a dark solid. This material was chromatographed (methylene chloride-hexanes: 1:2) to afford 4.15 g (78.4%) as a white solid: mp 106–°107.5 ° C.; IR (KBr) 3400 cm−1; MS EI m/e 263, 265,267, 269 (M+); $^1$H NMR (CDCl$_3$) δ 3.91 (2H, t, J=6.2 Hz), 4.33 (2H, t, J=6.2 Hz), 6.47 (1H, d, J=8.4 Hz), 7.08–7.13 (2H, m), 8.26 (1H, bs, NH).

Elemental analysis for $C_{22}H_{25}N_2O_3Cl$ Calc'd: C, 45.40; H, 3.05; N, 5.30 Found: C, 44.64; H, 2.74; N, 5.16

INTERMEDIATE 3

Method B 3,7-Dichloro-4-(2-chloroethoxy)-1H-indole

To a solution of 7-chloro-4-(2-chloroethoxy)-1H-indole (10.0 g, 37.8 mmol) in methanol (200 mL) under nitrogen containing sodium acetate (6.0 g) and acetic acid (1 mL) was added portionwise trichloroisocyanic acid (4.0 g, 17.2 mmol) at 2° C. The reaction temperature was maintained below 8° C. was allowed to stir for 4 hours at which time it was diluted with diethyl ether (200 mL) and washed with 10 NaOH. The organic layer dried over anhydrous magnesium sulfate, filtered and the solvent removed under vacuum to afford an oil. This material was dissolved in methylene chloride and filtered over a short pad of silica and concentrated to afford 10.0 g (87.0%) a yellowish white solid: mp 106°–107.5° C.; IR (KBr) 3400 cm−1; MS EI m/e 263, 265, 267, 269 (M+); $^1$H NMR (CDCl$_3$) δ 3.91 (2H, t, J=6.2 Hz), 4.33 (2H, t, J=6.2 Hz), 6.47 (1H, d, J=8.4 Hz), 7.08–7.13 (2H, m), 8.26 (1H, bs, NH).

INTERMEDIATE 4

N-2-Thienyl-[2-(3,7-dichloro-1H-Indol-4-yloxy)-ethyl]-ethylamine

A solution of the 2-(3,7-dichloro-1H-indol-4-yloxy)-chloroethane (1.70 g, 6.43 mmol) and 2-thienylmethylamine (2.91 g, 25.7 mmol) in anhydrous dimethylsulfoxide (6 mL) was heated to 90° C. for 12 hours. The reaction mixture was poured into water (150 mL) and made basic with 0.1N NaOH then extracted with methylene chloride (2×100 mL). The organic layers were combined and dried over anhydrous magnesium sulfate, filtered, and the solvent concentrated. Purfication with flash chromatography (ethyl acetate-hexanes: 1:1) afforded 1.68 g (76.3%) of an orangish solid: mp 99°–101° C.

Elemental analysis for $C_{15}H_{15}Cl_2N_2OS$ Calc'd; C, 52.79; H, 4.13; N, 8.21 Found: C, 52.70; H, 3.95; N, 8.19

(4b) N-3-Thienyl-[2-(3,7-dichloro-1H-indol-4-yloxy)-ethyl] -ethylamine was prepared similarly by using 3-thienylmethylamine and isolated as a yellow solid: mp 123°–125 ° C.; MS EI m/e 340/342/344 (M+).

Elemental analysis for $C_{18}H_{18}Cl_2N_2O$ Calc'd; C, 52.79; H, 4.14; N, 8.21 Found: C, 52.87; H, 4.05; N, 8.18

INTERMEDIATE 5

2,6-Dibromo-4-fluoro-phenol

To a solution of 4-fluorophenol (25 g, 0..22, mol) in acetic acid (200 mL) at room temperature was slowly added dropwise bromine (78 g, 0.49 mol) while being mechanically stirred. After 1 hour the reaction mixture was poured into ice water (1.5 L) followed by 100 mL of saturated aqueous sodium bisulfite. The solid precipitate was filtered and dried to afford 51.8 g (86.0%) a white solid: mp 54°–55 C.; $^1$H NMR (CDCl$_3$) δ 5.69 (1H, s, OH), 7.25 (2H, d, J=7.5 Hz); MS EI m/e 268/270/272 (M+).

Elemental analysis for $C_6H_3Br_2FO$ Calcd: C, 26.70; H, 1.12 Found: C, 26.64; H, 1.07

INTERMEDIATE 6

1-(2-Chloroethoxy)-2,6-dibromo-4-fluorobenzene

A mixture of 2,6-dibromo-4-fluoro-phenol (55 g, 0.20 mol), potassium carbonate (60 g, 0.43 mol), 1-bromo-2-chloroethane (32.5 g, 0.23 mol) and 2-butanone (500 mL) was heated to reflux for 2 hours and allowed to cool to ambient temperature. The solids were filtered and the solvent was removed under vacuum to afford an oil. The oil was dissolved in diethyl ether (300 mL) and washed with water, dried over anhydrous magnesium sulfate, charcaolized, and filtered through Solka floc to afford 65.9 g (97.2%) of an oil; MS EI m/e 330/332/334/336 (M+); $^1$H NMR (.CDCl$_3$) δ 3.89 (2H, t, J=6.1 Hz), 4.23 (2H, t, J=6.1 Hz), 7.28 (2H, d, J=7.5 Hz).

INTERMEDIATE 7

1-(2-Chloroethoxy)-2,6-dibromo-4-fluoro-3-nitrobenzene

To a solution of 1-(2-chloroethoxy)-2,6-dibromo-4-fluorobenzene (65.8 g, 0.20 mol) in concentrated sulfuric acid (165 mL) maintained at room temperature using a water bath was slowly added a solution of nitric acid in sulfuric acid (10 mL $HNO_3$ in 165 mL $H_2SO_4$). The reaction was allowed to stir at room temperature for 1 hour then poured into ice (1.5 L) and extracted with methylene chloride (2×300 mL). The combined organic layers were washed with aqueous sodium bicarbonate (150 mL) and dried over anhydrous magnesium sullfate, filtered, and the solvent removed under vacuum to afford 73.3 g (97.1%) a white crystalline solid: mp 56°–57 MS EI m/e 375/377/379/381; $^1$H NMR ($CDCl_3$) δ 3.91 (2H, t, J=5.9 Hz), 4.29 (2H, d, J=5.9 Hz), 7.54 (8.1 Hz).

Elemental analysis for $C_8H_5Br_2ClFNO_3$ Calcd: C, 25.46; H, 1.34; N, 3.71 Found: C, 25.46; H, 1.20; N, 3.51

INTERMEDIATE 8

1-(2-Chloroethoxy)-4-fluoro-3-aninobenzene

A solution of 1-(2-chloroethoxy)-2,6-dibromo-4-fluoro-3-nitrobenzene (73.2 g, 0.19 mol) in ethanol (1.1 L) containing 7.3 g of 10% palladium on carbon was hydrogenated at 40 psi for 5 days. The catalyst was filtered and the solvent was removed. The residue was dissolved in diethyl ether (300 mL) and washed with saturated aqueous sodium carbonate (200 L). The organic layer separated and washed with water, dried over anhydrous magnesium sulfate, filtered, and the solvent removed to afford an oil which solidies to afford 32.5 g (90.0%) a dark solid: mp 42°–43° C.; MS EI m/e 189/191 (M$^+$); 1H NMR ($CDCl_3$) δ 3.40–3.60 (2H, bs, $NH_2$), 3.77 (2H, d, J=6 Hz), 4.14 (2H, d, J=6 Hz), 6.19–6.23 (1H, m), 6.36 (1H, dd, J=7, 3 Hz), 6.88 (1H, dd, J=11, 9 Hz).

Elemental analysis for $C_8H_9ClFNO$ Calcd: C, 50.68; H, 4.78; N, 7.39 Found: C, 50.46; H, 4.66; N, 7.46

INTERMEDIATE 9

4-(2-Chloroethoxy)-7-fluoro-3-thiomethyl-1,3-dihydro-indol-2-one

To a solution of ethyl(methylthio)acetate (7.2 g, 53.4 mmol) in anhydrous methylene chloride (200 mL) at −78 ° C. was added sulfuryl chloride (8.1 g, 59.7 mmol) and stirred for 20 minutes. A solution of 1-(2-chloroethoxy)-4-fluoro-3-aminobenzene (10.0 g, 52.8 mmol) and Proton Sponge (13.9 g) in methylene chloride (100 mL) was added dropwise and stirred for 2 hours, followed by the addition of triethylamine (6.5 g, 64.5 mmol). The temperature was maintained at −78° C. and the reation mixture was allowed to stir for 1 hour. After warming to room temperature, the mixture was poured into brine (200 mL) and dried over anhydrous magnesium sulfate, filtered, and the solvent removed to afford an oil. Acetic acid (75 mL) was added to the oil and the mixture allowed to stand for 18 hours then the solvent was removed under vacuum. The residue was partitioned between diethyl ether (400 mL) and 2.5N aqueous hydrochloric acid (150 mL). The organic layer was separated and dried over anhydrous magnesium sulfate, filtered, and the solvent removed to afford a solid. Trituration of the solid with a small amount of diethyl ether (30 mL) afforded 8.8 g (60.5%) a yellow solid: mp 140–°141° C.; MS EI m/e 275/277 (M$^+$); $^1$NMR ($CDCl_3$) δ 2.14 (3H, s), 3.79–3.87 (2H, m), 4.25–4.33 (2H, m), 4.35 (1H, s), 6.51 (1H, dd, J=9.1, 3.3 Hz), 6.99 (1H, app. t, J=9.1 Hz), 8.09 (1H, s).

Elemental analysis for $C_{11}H_{11}ClFNO_2S$ Calcd: C, 47.92; H, 4.02; N, 5.08 Found: C, 47.67; H, 3.85; N, 4.85

EXAMPLE 1

4-[2-(3-Thienyl)-(aminoethoxy)]-7-fluoro-3-thiomethyl-1,3-dihydro-indol-2-one The title compound was prepared from 4-(2-chloroethoxy)-7-fluoro-3-thiomethyl-1,3-dihydro-indol-2-one (3.0 g, 10.9 mmol) and 3-thienylmethylamine (4.37 g, 38.6 mmol) in dimethylsulfoxide (50 mL) according to the procedure used to prepare intermediate 6 to afford 2.11 g (55%) of a tan oil: MS EI m/e 352 (M$^+$). The fumarate salt was prepared in ethanol to afford a white solid: mp 152.5–155 C; $^1$H NMR ($CDCl_3$) δ 1.93 (3H, s), 2.99 (2H, m), 3.93 (1 H, s), 4.11–4.20 (2H, m), 4.52 (1H, s), 6.55 (2H, s), 6.62 (1H, d, J=9,.3 Hz), 7.08–7.14 (2H, m), 7.41 (1H, m), 7.50 (1H, dd, J=5, 3 Hz), 11.00 (1H, bs); IR (KBr) 1710 cm−1.

Elemental analysis for $C_{16}H_{17}N_2FN_2O_2S_2 \cdot C_4H_4O_4$ Calc'd: C, 51.27; H, 4.52; N, 5.98 Found: C, 51.29; H, 4.52; N, 5.91

EXAMPLE 2

4-[2-(2-Thienyl-methyl-amino)-ethoxy]-7-chloro-1,3-dihydro-indol-2-one

To a solution of N-2-thienyl-[2-(3,7-dichloro-1H-Indol-4-yloxy)-ethyl]-ethylamine (1.41 g, 4.12 mmol) in 2-methoxyethanol (17 mL) was added phosphoric acid(4 mL). The solution was refluxed for 4 hours then poured into $H_2O$ (100 mL) and basified with 2.5N NaOH until pH 9. The aqueous layer was extracted with methylene chloride (2×200 mL). Combination of the organic layers, drying over $MgSO_4$ and evaporation of the solvent gave 1.15 g (86.5%) of product; mp 154°–155° C.

To a hot solution of fumaric acid (6.6 mmol)) in EtOH (20 mL) was added a hot solution of the product (1.08 g, 3.3 mmol) in EtOH (50 mL). This mixture was cooled, filtered and dried to give hemi-fumarate salt of the title compound as a slightly yellow white powder: 0.5429 g (60%); mp 203°–204° C.; MS EI m/e 323/324 (M$^+$).

Elemental analysis for $C_{15}H_{15}ClN_2SO_2 \cdot 0.5C_4H_4O_4$ Calcd: C, 53.61; H, 4.50; N, 7.36 Found: C, 53.41; H, 4.39; N, 7.17

(2b) 4-[2-(3-Thienyl-methyl-amino)-ethoxy]-7-chloro-1,3-dihydro-indol-2-one was prepared in the manner of the preceding Example 2 (40% yield). The fumarate salt was prepared from ethanol as a light brown solid: mp 191.5°–193° C.; MS EI m/e 323/324 (M$^+$).

Elemental analysis for $C_{15}H_{15}ClN_2SO_2 \cdot 0.5C_4H_4O_4$ Calcd: C, 53.61; H, 4.50; N, 7.36 Found: C, 53.27; H, 4.51; N, 7.17

EXAMPLE 3

4-[2-(3-Thienyl)-(aminoethoxy)]-7-fluoro-1,3-dihydro-indol-2-one

To a solution of 4-[(2-(3-thienyl)-(aminoethoxy)]-7-fluoro-3-thiomethyl-1, 3-dihydro-indol-2-one (1.80 g, 5.12 mmol) in ethanol (30 mL) was added intermittently an excess of Raney nickel at room temperature. After 5 hours the complete disappearance of starting material was observed and the catalyst was filtered and the solvent removed and the solid dissolved in a minimum amount of a solution of methanol in methylene chloride and passed through a silica gel column (5% methanol in methylene chloride) to afford 330 mg (21%) a light yellow solid; mp 154°–157 °C.; $^1$H NMR (DMSO-$d_6$) δ 2.80 (2H, t, J=6 Hz), 3.42 (2H, s), 3.74 (2H, s), 4.03 (2H, t, J=6 Hz), 6.54 (1H, d, J=9, 3 Hz), 7.01 (1H, app t, J=9 Hz)7.18–7.34 (5H, m), 10.81 (1H, d, J=10 Hz). The fumarate salt was prepared in ethanol to afford a yellow solid: mp 186.5°–187° C.

Elemental analysis for $C_{15}H_{15}FN_2O_2S \cdot 0.5\ C_2H_4O_4$ Calc'd: C, 56.03; H, 4.70; N, 7.69 Found: C, 55.81; H, 4.74; N, 7.34

(3b) 4-[2-(2-Thienyl)-(aminoethoxy)]-7-fluoro-1,3-dihydro-indol-2-one was prepared in the same manner as the product of Example 3. The fumarate salt was prepared from ethanol as yellow crystals: mp 184°–185.5° C. Elemental analysis for $C_{15}H_{15}FN_2O_2S \cdot 0.5\ C_2H_4O_4$ Calc'd: C, 56.03; H, 4.70; N, 7.69 Found: C, 55.48; H, 4.73; N, 7.48

Affinity for the dopamine autoreceptor was established by a modification of the standard experimental test procedure of Seemen and Schaus, European Journal of Pharmacology 203, 105–109 (1991), wherein homogenized rat striatal brain tissue is incubated with $^3$H-quinpirole (Quin.)and various concentrations of test compound, filtered and washed and counted in a Betaplate scintillation counter.

High affinity for the dopamine D-2 receptor was established by the standard experimental test procedure of Fields, et al., Brain Res., 136, 578 (1977) and Yamamura et al., eds., Neurotransmitter Receptor Binding, Raven Press, N.Y. (1978) wherein homogenized limbic brain tissue is incubated with $^3$H-spiroperidol (Spiper.) and various concentrations of test compound, filtered and washed and shaken with Hydrofluor scintillation cocktail (National Diagnostics) and counted in a Packard 460 CD scintillation counter.

The results of these studies were as follows:

| Example No. | $IC_{50}$ (nM) $D_2$ Quin. | $IC_{50}$ (nM) $D_2$ Spiper | Ratio |
| --- | --- | --- | --- |
| (1) | 1.49 | 135.3 | 91 |
| (2a) | 1.1 | 33.5 | 30.5 |
| (2b) | 0.71 | 26.7 | 37.7 |
| (3a) | 2.53 | 323 | 128 |
| (3b) | 1.36 | 398.4 | 293 |

Hence, the compounds of this invention effect the synthesis of the neurotransmitter dopamine and thus are useful in the treatment of dopaminergic disorders such as schizophrenia, Parkinson's disease, Tourette's Syndrome, alcohol addiction, cocaine addiction, and addiction to analagous drugs.

Applicable solid carriers for pharmaceutical compositions containing the compounds of this invention can include one or more substances which may also act as flavoring agents, lubricants, solubilizers, suspending agents, fillers, glidants, compression aids, binders or tablet-disintergrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific psychosis must be subjectively determined by the attending physician. The variables involved include the specific psychosis and the size, age and response pattern of the patient.

What is claimed is:

1. A compound of formula I

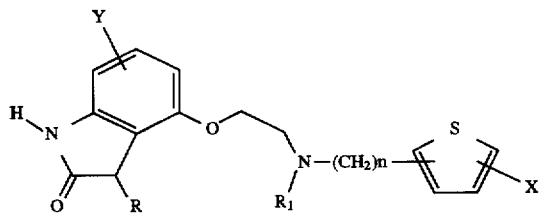

in which:

Y is hydrogen, halogen or alkoxy of 1 to 6 carbon atoms;

R is hydrogen or alkylthio of 1 to 6 carbon atoms;

$R_1$ is hydrogen or alkyl of 1 to 6 carbon atoms;

X is hydrogen, halogen, alkoxy of 1 to 6 carbon atoms, alkyl of 1 to 6 carbon atoms or phenyl;

n is one of the integers 1, 2, 3 or 4;

or a pharmaceutically acceptable salt thereof.

2. A compound of claim 1 in which Y is hydrogen, chloro or fluoro; R is hydrogen or alkylthio of 1 to 3 carbon atoms; R1 is hydrogen or alkyl of 1 to 3 atoms; X is hydrogen and n is on to the integers 2 and 3; or a pharmaceutically acceptable salt thereof.

3. The compound of claim 1 which is 4-[2-(3-thienyl)-(aminoethoxy)]-7-fluoro-3-thiomethyl-1,3-dihydro-indol-2-one or a pharmaceutically acceptable salt thereof.

4. The compound of claim 1 which is 4-[2-(2-thienyl-methyl-amino)-ethoxy]-7-chloro-1,3-dihydro-indol-2-one or a pharmaceutically acceptable salt thereof.

5. The compound of claim 1 which is 4-[2-(3-thienyl-methyl-amino)-ethoxy]-7-chloro-1,3-dihydro-indol-2-one or a pharmaceutically acceptable salt thereof.

6. The compound of claim 1 which is 4-[2-(3-thienyl)-(aminoethoxy)]-7-fluoro-1,3-dihydro-indol-2-one or a pharmaceutically acceptable salt thereof.

7. The compound of claim 1 which is 4-[2-(2-thienyl)-(aminoethoxy)]-7-fluoro-1,3-dihydro-indol-2-one or a pharmaceutically acceptable salt thereof.

8. A pharmaceutical composition of matter comprising a compound of the formula:

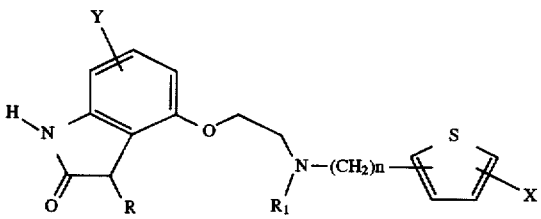

in which:

Y is hydrogen, halogen or alkoxy of 1 to 6 carbon atoms;
R is hydrogen or alkylthio of 1 to 6 carbon atoms;
$R_1$ is hydrogen or alkyl of 1 to 6 carbon atoms;
X is hydrogen, halogen, alkoxy of 1 to 6 carbon atoms, alkyl of 1 to 6 carbon atoms or phenyl;
n is one of the integers 1, 2, 3 or 4;

or a pharmaceutically acceptable salt thereof and a pharmaceutically acceptable carrier therefor.

9. A method for reducing dopamine synthesis and release in a patient suffering from hyperactivity of the dopaminergic systems, which comprises administering to said patient a compound of the formula:

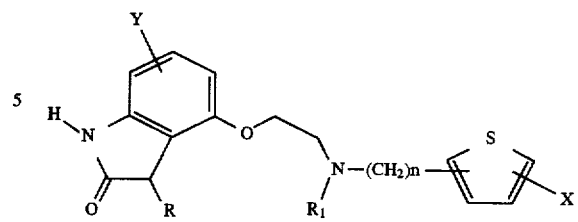

in which:

Y is hydrogen, halogen or alkoxy of 1 to 6 carbon atoms;
R is hydrogen or alkylthio of 1 to 6 carbon atoms;
$R_1$ is hydrogen or alkyl of 1 to 6 carbon atoms;
X is hydrogen, halogen, alkoxy of 1 to 6 carbon atoms, alkyl of 1 to 6 carbon atoms or phenyl;
n is one of the integers 1, 2, 3 or 4;

or a pharmaceutically acceptable salt thereof, in an amount sufficient to modulate the dopamine systems of the brain.

10. A method for treating schizophrenia which comprises administering to a patient suffering from schizophrenia, orally or parenterally, a compound of the formula:

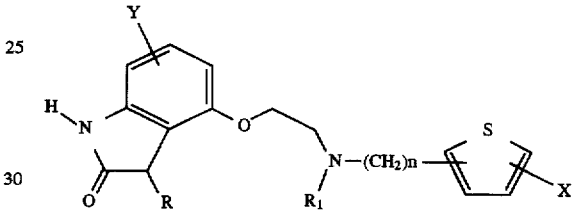

in which:

Y is hydrogen, halogen or alkoxy of 1 to 6 carbon atoms;
R is hydrogen or alkylthio of 1 to 6 carbon atoms;
$R_1$ is hydrogen or alkyl of 1 to 6 carbon atoms;
X is hydrogen, halogen, alkoxy of 1 to 6 carbon atoms, alkyl of 1 to 6 carbon atoms or phenyl;
n is one of the integers 1, 2, 3 or 4;

or a pharmaceutically acceptable salt thereof, in an amount sufficient to alleviate the symptoms of schizophrenia.

* * * * *